United States Patent [19]

Gillard et al.

[11] Patent Number: 4,871,756
[45] Date of Patent: * Oct. 3, 1989

[54] LEUKOTRIENE ANTAGONISTS

[75] Inventors: John Gillard, Pointe Claire; Joshua Rokach, Laval; Patrice C. Belanger, Dollard des Ormeaux, all of Canada

[73] Assignee: Merck Frosst Canada, Inc., Kirkland, Canada

[*] Notice: The portion of the term of this patent subsequent to May 19, 2004 has been disclaimed.

[21] Appl. No.: 15,823

[22] Filed: Feb. 17, 1987

Related U.S. Application Data

[60] Division of Ser. No. 713,927, Mar. 20, 1985, Pat. No. 4,667,055, which is a continuation-in-part of Ser. No. 566,858, Dec. 29, 1983, abandoned.

[51] Int. Cl.[4] .................. C07C 149/40; A61K 31/215
[52] U.S. Cl. .................................... 514/381; 514/459; 514/460; 514/471; 514/473; 514/517; 514/518; 514/520; 514/521; 514/522; 514/530; 514/562; 514/563; 514/567; 514/568; 514/571; 514/604; 514/605; 514/609; 514/617; 514/618; 514/619; 514/621; 514/684; 548/253; 549/426; 549/427; 549/475; 558/48; 558/405; 558/412; 558/413; 558/415; 560/9; 560/11; 560/12; 560/18; 560/21; 560/45; 560/53; 560/138; 562/426; 562/429; 562/430; 562/432; 562/435; 562/452; 562/455; 562/463; 564/88; 564/89; 564/92; 564/97; 564/99; 564/103; 564/162; 564/166; 564/167; 564/169; 568/64; 568/330; 549/426; 549/427; 549/475; 558/48; 558/405; 558/412; 558/413; 558/415; 560/9; 560/11; 560/12; 560/18; 560/21; 560/45; 560/53; 560/138; 562/426; 562/429; 562/430; 562/432; 562/435; 562/452; 562/455; 562/463

[58] Field of Search .................... 560/9, 11, 12, 27, 45, 560/18, 21, 53, 138; 562/426, 429, 430, 452, 455, 463, 432, 435; 514/486, 539, 545, 562, 563, 568, 381, 459, 460, 471, 473, 517, 518, 520, 521, 522, 530, 567, 571, 604, 605, 609, 617, 618, 619, 621, 684; 548/253; 549/426, 427, 425; 558/48, 405, 412, 413, 415; 564/88, 89, 92, 97, 99, 103, 162, 166, 167, 169; 568/64, 330

[56] References Cited

U.S. PATENT DOCUMENTS

| 3,970,694 | 7/1976 | Manai | 562/469 |
| 4,008,323 | 2/1977 | Cousse | 514/570 |
| 4,133,889 | 1/1979 | Augstein | 562/463 |

FOREIGN PATENT DOCUMENTS

| 56172 | 7/1982 | European Pat. Off. . |
| 61800 | 10/1982 | European Pat. Off. . |
| 56-25149 | 3/1981 | Japan | 560/11 |
| 2058785 | 4/1981 | United Kingdom . |

OTHER PUBLICATIONS

Bailey, Ann. Rpts. Med. Chem., 17, p. 203 (1982).
Samuelsson, Science, 220, p. 568 (1983).

Primary Examiner—Michael L. Shippen
Attorney, Agent, or Firm—Gabriel Lopez; Hesna J. Pfeiffer

[57] ABSTRACT

Compounds having the formula:

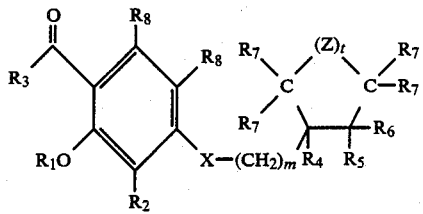

are antagonists of leukotrienes of $C_4$, $D_4$, $E_4$ and the slow reacting substance of anaphylaxis.

As such, these compounds will be useful as anti-asthmatic, anti-allergic, anti-inflammatory and cytoprotective agents.

8 Claims, No Drawings

LEUKOTRIENE ANTAGONISTS

This is a division of application Ser. No. 713,927, filed 3/20/85 now U.S. Pat. No. 4,667,055, which is a continuation-in-part of U.S. Ser. No. 566,858, filed Dec. 29, 1983, now abandoned, the disclosure of which is hereby incorporated herein by reference.

This invention is directed to compounds which act as antagonists of the leukotrienes.

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis (SRS-A).

The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene $B_4$, a dihydroxy fatty acid. This compound is a potent chemotactic agent for neutrophils and eosinophils and in addition, may modulate a number of other functions of these cells. It also effects other cell types such as lymphocytes and for example may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., Ann. Rpts. Med. Chem. 17 203 (1982).

The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthamatic lungs. 5-Lipoxygenase products are also thought to be regulators of mast cell degranulation and recent studies with human lung mast cells have suggested that 5-lipoxygenase inhibitors, but not corticosteroids, may suppress antigen-induced mast cell degranulation. In vitro studies have shown that antigen challenge of human lung results in the release of leukotrienes and in addition purified human mast cells can produce substantial amount of leukotrienes. There is therefore good evidence that leukotrienes are important mediators of human asthma. Leukotriene antagonists would therefore be a new class of drugs for the treatment of asthma.

Psoriasis is a human skin disease which effects between two and six percent of the population. There is no adequate therapy for psoriasis and related skin conditions. The evidence for leukotriene involvement in these diseases is as follows. One of the earliest events in the development of preparpillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in uninvolved skin, in biologically significant amounts.

Leukotrienes can be measured in nasal washings from patients with allergic rhinitis and are greatly elevated following antigen challenge. Leukotrienes may mediate this disease through their ability to regulate mast cell degranulation, by modulating mucous production and mucociliary clearance and by mediating the accumulation of inflammatory leukocytes.

Leukotrienes can also mediate other diseases. These include atopic dermatitis, gouty arthritis and gall bladder spasms. In addition, they may have a role in cardiovascular disease because leukotrienes $C_4$ and $D_4$ act as coronary and cerebral arterial vasoconstrictors and these compounds may also have negative inotropic effects on the myocardium. In addition, the leukotrienes are important mediators of inflammatory diseases through their ability to modulate leukocyte and lymphocyte function. See for example, B. Samuelsson, Science, 220, 568 (1983).

Several classes of compounds exhibit the ability to antagonise the actions of leukotrienes in mammals. See for example, Great Britain Patent Specification No. 2,058,785; and European Patent Application Nos. 56,172 and 61,800.

The present invention provides compounds that act as antagonists to prevent leukotriene action. The present invention also provides compounds which prevent or reverse leukotriene action or prevent leukotriene synthesis when administered orally. The present invention also provides compounds which prevent or reverse leukotriene action when administered by insufflation, intravenously, rectally, topically, parenterally including subcutaneously and intramuscularly, or nasally. The present invention also provides methods for the preparation of these compounds. The present invention also provides intermediates useful in the synthesis of these compounds. Finally, the present invention provides pharmaceutical formulations for administering these compounds.

The compounds of the present invention have the formula:

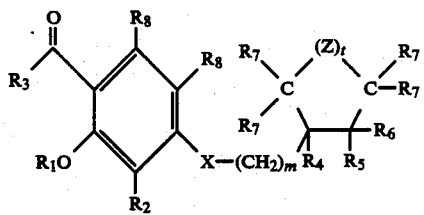

wherein:

$R_1$ is H, alkyl of 1 to 6 carbon atoms, $R_3$—CO—, or $R_3OCH_2$—;

$R_2$ is alkyl of 1 to 6 carbon atoms which may be straight chain or branched or alkenyl of 3 to 6 carbon atoms, which may be straight chain or branched;

$R_3$ is H or alkyl of 1 to 6 carbon atoms;

$R_4$ is H; $OR_1$ provided that m is 1; or —(CH$_2$)$_n$—Y—C$_6$H$_3$R$_8$R$_9$, provided that m and n are not both zero;

$R_5$ is —(CH$_2$)$_n$—Y—C$_6$H$_3$R$_8$R$_9$;

$R_6$ is H; $OR_1$; or —(CH$_2$)$_n$—Y—C$_6$H$_3$R$_8$R$_9$;

each $R_7$ is independently H or alkyl of 1 to 6 carbon atoms;

each $R_8$ is independently H; OH; alkyl of 1 to 6 carbon atoms; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; $N(R_7)_2$; benzyl; phenethyl; halogen; $COOR_7$; $CH_2OR_7$; formyl; CN; trifluoromethylthio; or nitro;

$R_9$ is:

$$-\overset{Z'}{\underset{R_{11}}{\overset{\|}{C}}}-(C)_r\!\!\begin{bmatrix}R_{12}\\ | \\ C\!=\!=\!=\!C\\ | \\ R_{11}\end{bmatrix}_p\!\!(C)_q\!-R_{13}$$

wherein the broken line represents an optional triple bond and Z' is O; S; CH$_2$; H and OH; alkenyl of 1 to 4 carbons; or N-R$_{14}$;

each $R_{10}$ is independently H or alkyl of 1 to 4 carbons;

each $R_{11}$ is independently H, OH, or alkyl of 1 to 4 carbons;

each $R_{12}$ is independently H, or alkyl of 1 to 4 carbons, and is absent when a triple bond is present;

$R_{13}$ is $COOR_7$; $CH_2OH$; CHO; tetrazole; $NHSO_2R_{14}$; $CONHSO_2R_{14}$; hydroxymethylketone; CN; $CON(R_7)_2$; a monocyclic or bicyclic heterocyclic ring containing an acidic hydroxyl group; or $COOR_{15}$ where $R_{15}$ is:

$$-(CH_2)_s-\overset{R_{10}}{\underset{R_{10}}{C}}(CH_2)_s-R_{16}$$

independently 0 to 3; $R_{16}$ is (A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or (B) the radical W-R$_{17}$ wherein W is O, S or NH and R$_{17}$ contains up to 21 carbon atoms and is (1) a hydrocarbon radical or (2) an acyl radical of an organic acyclic or monocyclic carboxylic acid containing not more than 1 heteroatom in the ring;

each $R^{14}$ is independently OH, alkyl or alkoxy of 1 to 6 carbon atoms, perhaloalkyl of 1 to 6 carbon atoms, phenyl or phenyl substituted by alkyl or alkoxy groups of 1 to 3 carbon atoms, halogen, hydroxy, haloalkyl, COOH, CN, formyl or acyl of 1 to 6 carbon atoms;

X is O, S, SO or SO$_2$;

each Y is independently O; S; SO; SO$_2$;

$$\overset{O}{\underset{}{\overset{\|}{S}}}=NR_7;\quad \overset{O}{\underset{}{\overset{\|}{N-C}}}-R_{18};$$

or N—CN;

Z is =C(R$_7$)$_2$, O, S, SO, SO$_2$, NR$_3$ or $$\overset{O}{\underset{}{\overset{\|}{=NC}}}-R_{18};\quad H;\quad R_6$$

each $R_{18}$ is independently alkyl of 1 to 4 carbon atoms, alkoxy of 1 to 4 carbon atoms, which may be straight chain or branched;

m is 0 or 1;

n is 0 or 1 provided that both m and n are not 0, or that both m and n are not 1;

independently 0 to 3; $R_{16}$ is (A) a monocyclic or bicyclic heterocyclic radical containing from 3 to 12 nuclear carbon atoms and 1 to 2 nuclear heteroatoms selected from N and S with at least one being N, and with each ring in the heterocyclic radical being formed of 5 or 6 atoms, or (B) the radical W-R$_{17}$ wherein W is O, S or NH and R$_{17}$ contains up to 21 carbon atoms and is (1) a hydrocarbon radical or (2) an acyl radical of an organic acyclic or monocyclic carboxylic acid containing not more than 1 heteroatom in the ring;

each $R^{14}$ is independently OH, alkyl or alkoxy of 1 to 6 carbon atoms, perhaloalkyl of 1 to 6 carbon atoms, phenyl or phenyl substituted by alkyl or alkoxy groups of 1 to 3 carbon atoms, halogen, hydroxy, haloalkyl, COOH, CN, formyl or acyl of 1 to 6 carbon atoms;

X is O, S, SO or SO$_2$;

each Y is independently O; S; SO; SO$_2$;

$$\overset{O}{\underset{}{\overset{\|}{S}}}=NR_7;\quad \overset{O}{\underset{}{\overset{\|}{N-C}}}-R_{18};$$

or N—CN;

Z is =C(R$_7$)$_2$, O, S, SO, SO$_2$, NH$_3$ or $$\overset{O}{\underset{}{\overset{\|}{=NC}}}-R_{18};$$

each $R_{18}$ is independently alkyl of 1 to 4 carbon atoms, alkoxy of 1 to 4 carbon atoms, which may be straight chain or branched;

m is 0 or 1;

n is 0 or 1 provided that both m and n are not 0, or that both m and n are not 1;

t is 1 to 4, provided that when t is greater than 1, all but one of the resulting Z units must be —C(R$_7$)$_2$;

p is 0 or 1;

q and r are each independently 0 to 20 provided that the total of q and r does not exceed 20; and pharmaceutically acceptable salts thereof.

A preferred class of compounds have the formula II:

wherein:
R$_2$ is as defined for formula I
R$_3$ is as defined for formula I
R$_4$ is H; OH, provided that m is 1; or

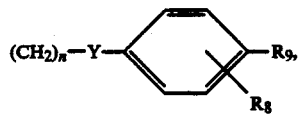

provided that both m and n are not zero;
R$_5$ is H; OH, provided that R$_6$ is not OR$_1$; or

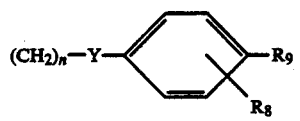

R$_6$ is H; OH; or

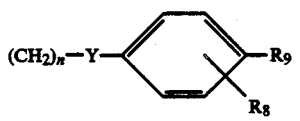

R$_7$ is as defined for formula I
R$_8$ is as defined for formula I
R$_9$ is

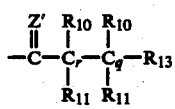

wherein:
Z' is O; H and OH;
R$_{10}$ and R$_{11}$ are as defined for I;
R$_{13}$ is COOR$_7$; CH$_2$OH; CHO; or tetrazole;
r and q are each independently 0 to 5;
X is as defined for formula I;
Y is O, S, SO or SO$_2$;
t is 1 to 4; and
m and n are as defined for formula I.

The term alkyl refers to a saturated hydrocarbon unit of the indicated number of carbon atoms which may be straight chain, branched chain or cyclic in structure.

The compounds disclosed herein may contain one or more centers of asymmetry. In those instances when assymetric carbon atoms are present, more than one stereoisomer is possible, and all possible isomeric forms are deemed to be included within the planar structural representations shown. Optically active (R) and (S) isomers may be resolved using conventional techniques known to the skilled artisan. The present invention is meant to include the possible diastereomers as well as the racemic and optically resolved isomers.

The compounds of the present invention are useful as anti-asthmatic, anti-allergic, and anti-inflammatory agents and are useful in treating allergic rhinitis and chronic bronchitis and for ameliorating skin diseases like psoriasis and atopic eczema. These compounds are also useful to antagonize or inhibit the effects of the leukotrienes on the cardiovascular and vascular systems. It should be understood that in this paragraph and in the discussion of methods of treatment and pharmaceutical compositions which follows, references to the compounds of Formula I, unless indicated otherwise, are meant to include the corresponding pharmaceutically acceptable salts.

The compounds of the present invention may also be used to treat or prevent mammalian (especially, human) disease states such as erosive gastritis; erosive esophagitis; inflammatory bowel disease; ethanol-induced hemorrhagic rosions; hepatic ischemia; noxious agent induced damage or necrosis of hepatic, pancreatic, renal, or myocardial tissue; liver parenchymal damage caused by hepatoxic agents such as CCl$_4$ and D-galactosamine; ischemic renal failure; disease-induced hepatic damage; bile salt induced pancreatic or gastric damage; trauma- or stress-induced cell damage; and glycerol-induced renal failure.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cyto-protective ability. These assays are; (A) an ethanol-induced lesion assay and (B) an indomethacin-induced ulcer assay.

A. Ethanol-Induced Gastric Ulcer

Twenty-four hour fasted Sprague-Dawley (S.D.) rats are perorally (p.o.) dosed with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosae are examined for resulting lesions.

B. Indomethacin-Induced Ulcer Assay

Indomethacin, 10 mg/kg p.o., is used to induce ulcers in 24 hour fasted S.D. rats. Fifteen minutes prior to indomethacin administration, groups of rats each receive either an aqueous vehicle (5% by weight methylcellulose) or the test compound at various doses perorally. Four hours later the animals are sacrificed and stomach mucosae are examined for resulting ulcers.

The magnitude of a prophylactic or therapeutic dose of a compound of formula I will, of course, vary with the nature of the severity of the condition to be treated and with the particular compound of formula I and its route of administration. In general, the daily dose range for anti-asthmatic, anti-allergic or anti-inflammatory use lies within the range of from about 0.2 mg to about 100 mg per kg body weight of a mammal.

The exact amount of a compound of the Formula I to be used as a cytoprotective agent will depend on, inter alia, whether it is being administered to heal damaged cells or to avoid future damage, on the nature of the damaged cells (e.g., gastro-intestinal ulcerations vs. nephrotic necrosis), and on the nature of the causative agent.

The effective daily dosage level for compounds of Formulae I inducing cytoprotection in mammals, especially humans, will generally range from about 0.002 mg/kg to about 100 mg/kg, preferably from about 0.02 mg/kg to about 30 mg/kg. The dosage may be administered in single or divided individual doses.

Any suitable route of administration may be employed for providing a mammal, especially a human with an effective dosage of a leukotriene antagonist. For example, oral, rectal, transdermal, parenteral, intramuscular, intravenous and the like may be employed. Dosage forms include tablets, troches, dispersions, suspensions, solutions, capsules and the like.

The pharmaceutical compositions of the present invention comprise a compound of formula I as an active ingredient or a pharmaceutically acceptable salt thereof, and may also contain a pharmaceutically acceptable carrier and optionally other therapeutic ingredients. the term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

The pharmaceutical compositions of the present invention include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use is from about 0.2 mg to about 20 mg (preferably from about 1 mg to about 10 mg) of a compound of formula I per kg of body weight per day and for cytoprotective use from about 0.002 mg to about 100 mg (preferably from about 0.02 mg to about 30 mg and more preferably from about 0.1 mg to about 10 mg) of a compound of Formula I per kg of body weight per day. In the case where an oral composition is employed, a suitable dosage range for anti-asthmatic, anti-inflammatory or anti-allergic use is, e.g. from about 1 to about 100 of a compound of formula I per kg of body weight per day, preferably from about 5 mg to about 40 mg per kg and for cytoprotective use from about 0.01 mg to about 100 mg (preferably from about 0.1 mg to about 30 mg and more preferably from about 0.1 mg to about 10 mg) of a compound of Formula I per kg of body weight per day.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, leukotriene antagonists of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; cr carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the leukotriene antagonists of Formula I may also be administered by controlled release means and/or delivery devices such as those described in U.S. Pat. Nos. 3,845,770; 3,916,899; 3,536,809; 3,598,123; 3,630,200 and 4,008,719, the disclosure of which is hereby incorporated herein by reference.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active compound of formula I.

The following are examples of representative pharmaceutical dosage forms for the leukotriene antagonists of Formula I:

| Injectable Suspension | mg/ml |
|---|---|
| Compound of Formula I | 2 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of | 1 ml |

| Tablet | mg/tablet |
|---|---|
| Compound of Formula I | 25.0 |
| Microcrystalline Cellulose | 415.0 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

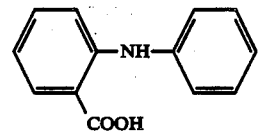

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

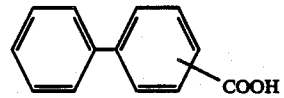

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

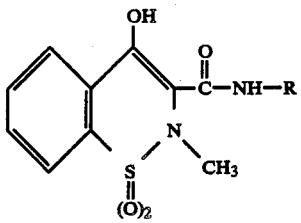

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, WY41770.

Finally, NSAIDs which may also be used include the salicylates, specifically aspirin, and the phenylbutazones, and pharmaceutically acceptable salts thereof.

Pharmaceutical compositions comprising the Formula I compounds may also contain inhibitors of the biosynthesis of the leukotrienes such as are disclosed in pending U.S. Patent Application Ser. No. 539,342, filed Oct. 5, 1983, now abandoned, Ser. No. 459,924, filed Jan. 21, 1983, now abandoned, Ser. No. 539,215, filed Oct. 5, 1983, now abandoned, and Ser. No. 547,161, filed Oct. 31, 1983, now abandoned, which are hereby incorporated herein by reference.

The compounds of the Formula I may also be used in combination with leukotriene antagonists such as those disclosed in copending applications U.S. Ser. Nos. 520,051 and 520,052, filed Aug. 5, 1983, now abandoned, which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application No. 11,067 or thromboxane antagonists such as those disclosed in U.S. Pat. No. 4,237,160. They may also contain histidine decarboxyase inhibitors such as α-fluoromethylhistidine, described in U.S. Pat. No. 4,325,961. The compounds of the Formula I may also be advantageously combined with an $H_1$ or $h_2$-receptor antagonist, such as for instance cimetidine, ranitidine, terfenadine, famotidine, aminothiadiazoles disclosed in EP No. 40,696 and like compounds, such as those disclosed in U.S. Pat. Nos. 4,283,408; 4,362,736; 4,394,508. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

SCHEME I

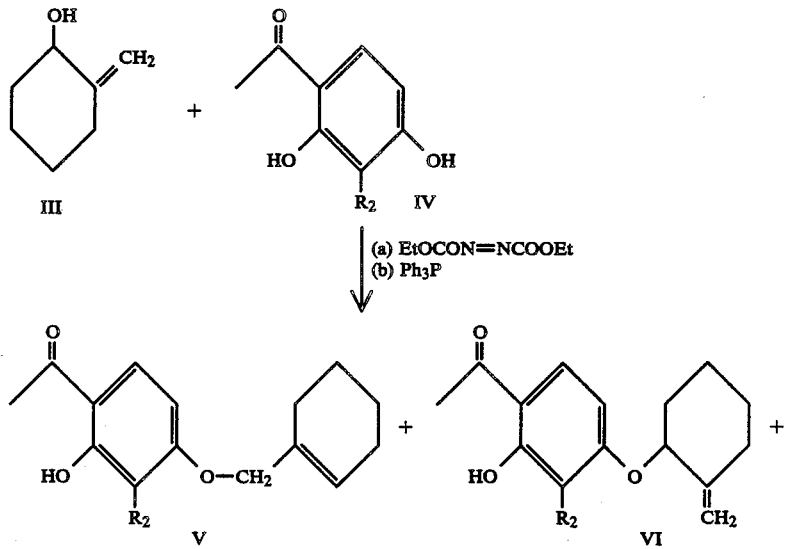

SCHEME I
-continued
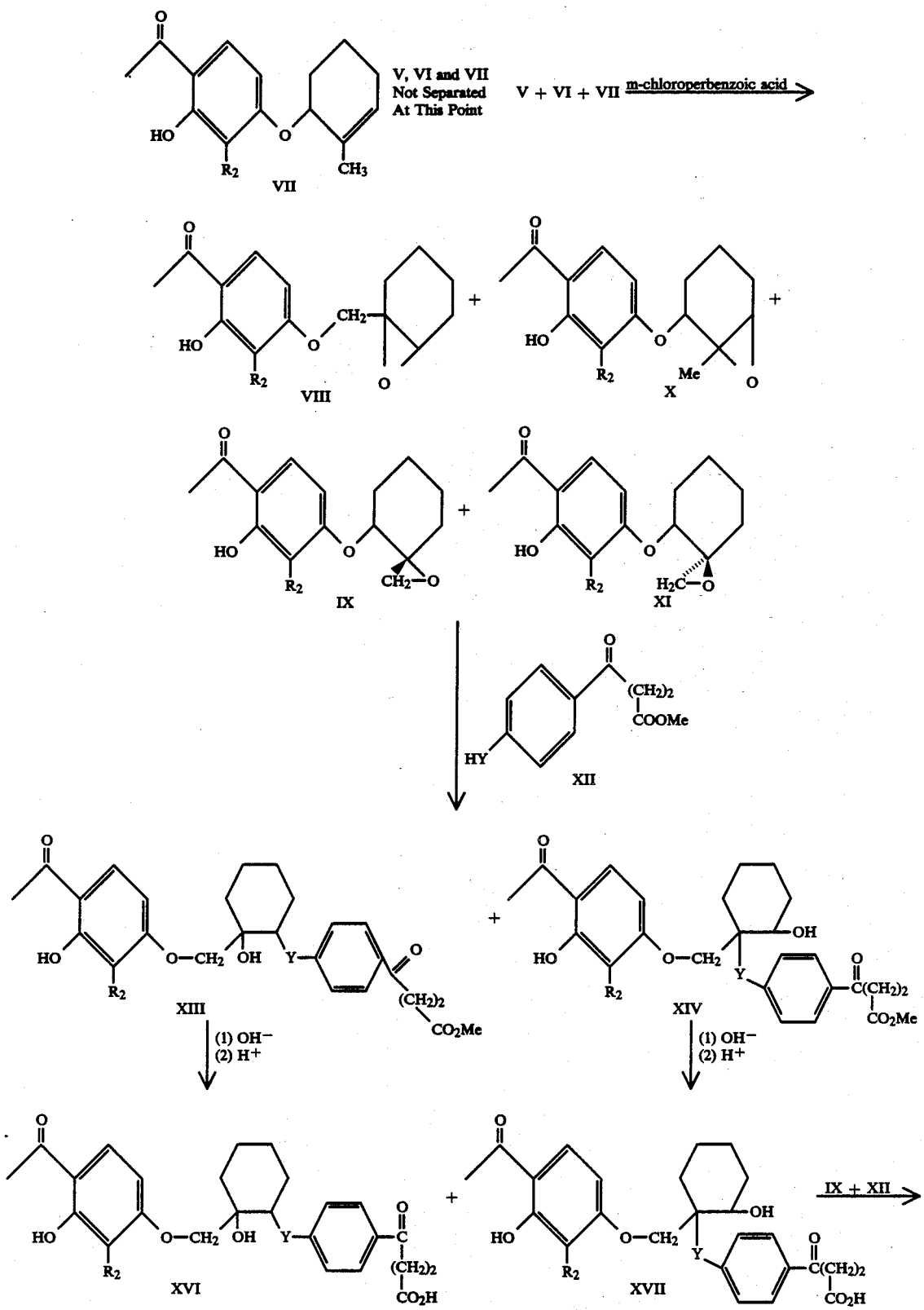

-continued
SCHEME I

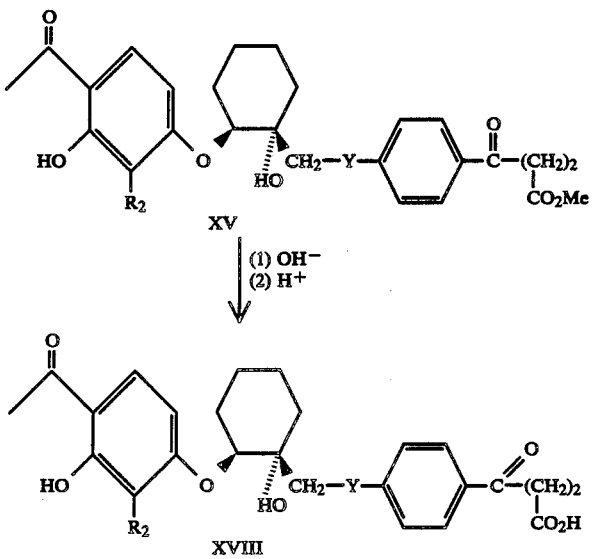

The compounds of the present invention may be prepared by several different routes. According to one method, illustrated in Scheme I, 2-methylene cyclohexanol (III) may be reacted with a 2,4-dihydroxy-3-alkylacetophenone (IV) using diethylazodicarboxylate (DEAD) and triphenylphosphine according to the method of O. Mitsumobo, *Synthesis* 1 (1981) to yield the mixture of intermediate compounds having the formulae V, VI and VII.

Compounds V, VI and VII may be epoxidized by reaction with a peracid, for example, m-chloroperbenzoic acid to yield the mixture of epoxides having formulae VIII, IX, X and XI.

Compounds VIII or IX may be reacted with a suitably substituted aromatic alcohol or mercaptan of formula XII (Y=O,S) to yield the species having the formulae XIII, XIV or XV.

Conventional hydrolysis of compounds XIII, XIV or XV yields compounds having the formulae XVI, XVII or XVIII respectively, which are representative Formula I compounds.

When Y is sulfur, oxidation of the compound with one or more equivalents of an oxidizing agent, for example, m-chloroperbenzoic acid, $H_2O_2$ in acetic acid, and the like, yields the corresponding sulfoxide or sulfone of the Formula I compound.

Guinea Pig Ileum Assay for Evaluation of Antagonists of Leukotriene $D_4$ and Other Mediators The terminal ileum from male Hartley strain guinea pigs (300–500 g) was removed and suspended under 1 g resting tension in Tyrode's solution containing $1.0 \times 10^{-6}$ M atropine sulfate and $1.6 \times 10^{-6}$ M timolol (beta blocker). After a 15–30 minute stabilization period, a standard dose of leukotriene $D_4$ (0.3 ng/ml—final bath concentration) was added repeatedly until consistent and reproducible contractile responses were obtained. Isometric contractions to leukotriene $D_4$ were recorded for 60 seconds and then the tissue was washed and allowed to recove to baseline (2 minutes) before the next dose of leukotriene $D_4$ was added. For testing antagonist compounds, a 30 second pretreatment period was used and the percent inhibition of the control contraction to leukotriene $D_4$ was recorded. A similar procedure was employed for testing active compounds against contractions to a standard dose of histamine (50 ng/ml—final bath concentration).

The antagonist activity of selected Formula I compounds is presented below in Table I.

TABLE I

Inhibition of Ileum Contraction Induced by $LTD_4$

| Compound | Concentration | % Inhibition |
|---|---|---|
| 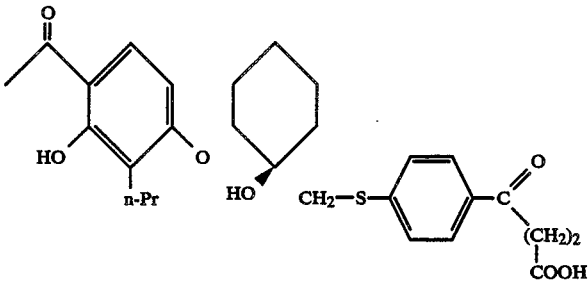 L-649,103 | 10 μg/ml | 62% |

TABLE I-continued
Inhibition of Ileum Contraction Induced by LTD₄

| Compound | Concentration | % Inhibition |
|---|---|---|
| L-649,106 | 10 μg/ml | 80% |
|  | 1 μg/ml | 23% |
| L-649,107 | 10 μg/ml | 12% |

The following examples are provided to more fully illustrate the preparation of the compounds of the present invention. These examples are merely illustrative in nature and are not intended to limit the scope of the invention. All temperatures are expressed in degrees Celsius.

EXAMPLE 1

Preparation of trans-2-(4-acetyl-3-hydroxy-2-propyl phenoxy)-1-(4-(3-carboxy-1-oxopropyl)phenylthiomethyl)cyclohexanol

Step A

2-Methylene cyclohexanol

The title compound was prepared by the rearrangement of 1-methyl-1,2-epoxycyclohexane with lithium diisopropylamide in ether as described in J. Org. Chem. 33 2375 (1968).

Step B

2-Methylene-1-(4-acetyl-3-hydroxy-2-propyl phenoxy)cyclohexane

A solution of triphenyl phosphine (22 g; 87 mmoles) in THF (50 ml) was added to a solution of 2-methylene cyclohexanol (13 g: 50 mmoles) 3-propyl-2,4-dihydroxy acetophenone (11.25 g: 58 mmoles), diethylazodicarboxylate (15.1 g: 87 mmoles) in THF (500 ml) cooled to 0° C. The reaction mixture was stirred at 0° C. for 1 hour. It was then concentrated in vacuo and the residue was slurried in a mixture of 10% ethyl acetate in hexane (300 ml). The resulting triphenyl phosphine oxide was filtered off and the filtrate was reduced in vacuo to a small volume. Chromatography on silica gel, eluting with 10% EtOAc/hexane gave 7.8 g of the title compound contaminated by about 30% of isomeric 1-(4-acetyl-3-hydroxy-2-propylphenoxymethyl)cyclohexane and by 6-(4-acetyl-3-hydroxy-2-propylphenoxy)-1-methyl cyclohexene.

This material was not purified further and was used as such in Step C.

Step C

1-(4-acetyl-3-hydroxy-2-propylphenoxymethyl)-1,2-epoxycyclohexane; cis and trans 2-(4-acetyl-3-hydroxy-2-propylphenoxy)1-methyleneepoxycyclohexane and 6-(4-acetyl-3-hydroxy-2-propylphenyloxy)-1-methyl-1,2-epoxycyclohexane The mixture of olefins from Step B of this example (2.0 g; 6.9 mmoles) in methylene chloride (150 ml) and 1N sodium bicarbonate (75 ml) was treated with 85% m-chloroperbenzoic acid (8.75 mmoles) at 0°-5° C. for 90 minutes. The reaction mixture was stirred at room temperature overnight. The organic layer was separated and treated with calcium hydroxide (5 g) for 15 minutes. The mixture was filtered and the filtrate was concentrated in vacuo. The residue was chromatographed on silica gel, eluting with 10% ethyl acetate-hexane to yield successively.

1. cis-2-(4-acetyl-3-hydroxy-2-propylphenoxy)-1-methyleneepoxycyclohexane.

Anal. calcd. C, 71.02; H, 7.94. Found: C, 70.95; H, 7.96.

2. trans-2-(4-acetyl-3-hydroxy-2-propylphenoxy-1-methyleneepoxycyclohexane.

Anal. calcd. C, 71.02; H, 7.94. Found: C, 70.96; H, 7.87.

3. 1-(4-acetyl-3-hydroxy-2-propylphenoxymethyl)-1,2-epoxycyclohexane.

Anal. calcd. C, 71.02; H, 7.94. Found: C, 70.96; H, 7.87.

4. 6-(4-acetyl-3-hydroxy-2-propylphenoxy)-1-methyl-1,2-epoxycyclohexane, m.p. 50°–52° C.

Anal. calcd. C, 71.02; H, 7.94. Found: C, 70.98; H, 7.92.

Step D

Trans 2-(4-acetyl-3-hydroxy-2-propylphenoxy)-1-(4-(3-carbomethoxy-1-oxopropyl)phenylthiomethyl)cyclohexanol The epoxide 2 of Step C (608 mg; 2 mmoles) was added to a solution of the sodium salt of methyl 4-mercaptobenzene-gamma-oxobutyrate in methanol (15 ml) and the reaction mixture was refluxed for 7 hours and then stirred at room temperature for 72 hours. The reaction mixture was concentrated in vacuo and the residue was partitioned between ethyl acetate and a saturated solution of ammonium chloride. The organic layer was dried ($Na_2SO_4$) and concentrated in vacuo to give a residue that was chromatographed on silica gel. Elution with 50% ethyl acetate-hexane afforded 450 mg of the title compound, m.p. 133°–135° C.

Anal. calcd. C, 65.88; H, 6.86; S, 6.06. Found: C, 65.49; H, 6.95; S, 6.51.

Step E

Trans 2-(4-acetyl-3-hydroxy-2-propylphenoxy)-1-(4-(3-carboxy-1-oxopropyl)phenylthiomethyl)cyclohexanol The ester obtained in Step D of this example (350 mg; 0.66 mmole) was stirred at room temperature in a mixture of methanol (10 ml) and in sodium hydroxide (2.5 ml) for 2 hours. The volatiles were removed in vacuo, the residue was taken up in water and the solution was acidified with dilute hydrochloric acid. The solid was filtered, washed with water and air-dried to yield 250 mg (73%) of the title compound, m.p. 86°–89° C.

Anal. calcd. C, 65.34; H, 6.65; S, 6.23. Found: C, 65.09; H, 6.80; S, 6.24.

EXAMPLE 2

Preparation of 1-(4-acetyl-3-hydroxy-2-propylphenoxymethyl)-2-(4-(3-carboxy-1-oxopropyl)phenylthio)cyclohexanol

Step A 1-(4-Acetyl-3-hydroxy-2-propylphenoxymethyl)-2-(4-(3-carbomethoxy-1-oxopropyl)phenylthio)cyclohexanol The epoxide 3 of Step C of example 1 (5.93 mg; 1.95 mmoles) was added to a solution of the sodium salt of methyl 4-mercapto benzene-gamma-oxo-butyrate as described in Step D of Example 1, to afford 200 mg of the title compound as an oil.

Isomeric 2-(4-acetyl-3-hydroxy-2-propylphenoxymethyl)-2-(4-(3-carbomethoxy-1-oxopropyl)phenylthio)-cyclohexanol (200 mg) was also obtained as an oil.

Step B 1-(4-acetyl-3-hydroxy-2-propylphenoxymethyl)-2-(4-(3-carboxy-1-oxopropyl)phenylthio)cyclohexanol The title compound of Step A of Example 2 was hydrolyzed in a manner similar to that described in Step E of Example 1, to afford the title compound, m.p. 55°–57° C. and remelts at 127°–129° C.

EXAMPLE 3

Preparation of 2-(4-acetyl-3-hydroxy-2-propylphenoxymethyl)-2-(4-(3-carboxy-1-oxopropyl)phenylthio)cyclohexanol The isomer of the title compound of Step A of Example 2 was treated with sodium hydroxide as described in Step E of Example 1 to afford the title compound, m.p. 65°–67°, remelts at 125°–127° C.

Anal. calcd. C, 65.34; H, 6.65; S, 6.23. Found: C, 65.25; H, 6.82; S, 6.65.

What is claimed is:

1. A compound of the formula:

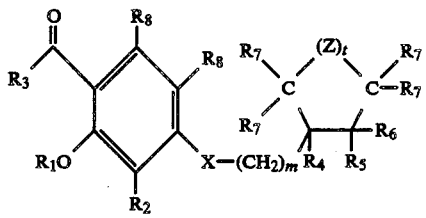

wherein:

$R_1$ is H, alkyl of 1 to 6 carbon atoms, $R_3$-CO-, or $R_3OCH_2-$;

$R_2$ is alkyl of 1 to 6 carbon atoms which may be straight chain or branched, alkenyl of 3 to 6 carbon atoms, which may be straight chain or branched;

$R_3$ is H or alkyl of 1 to 6 carbon atoms;

$R_4$ is H; $OR_1$ provided that m is 1; or

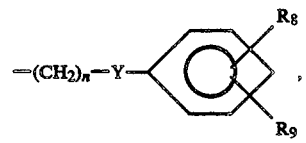

provided that m and n are not both zero;

$R_5$ is H; $OR_1$, provided that $R_6$ is not $OR_1$; or

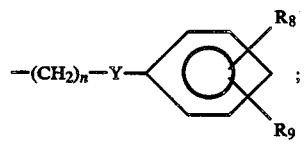

$R_6$ is H; $OR_1$; or

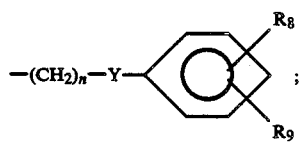

with the proviso that not all of R₄, R₅ and R₆ are simultaneously

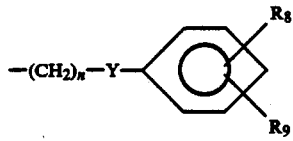

but at least one must be OH;
each R₇ is independently H or alkyl of 1 to 6 carbon atoms;
each R₈ is independently H; OH; alkyl of 1 to 6 carbon atoms which may be straight chain or branched; alkenyl of 2 to 6 carbon atoms which may be a straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen; N(R₇)₂; COOR₇; CH₂OR₇; formyl; CN; trifluoromethylthio; or nitro;
R₉ is

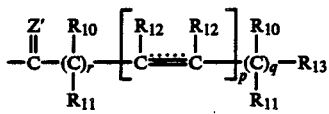

wherein the broken line represents an optional triple bond and Z' is O; S; CH₂; H and OH; alkenyl of 1 to 4 carbons; or N—R₁₄;
each R₁₀ is independently H or alkyl of 1 to 4 carbons;
each R₁₁ is independently H, OH, or alkyl of 1 to 4 carbons;
each R₁₂ is independently H, or alkyl of 1 to 4 carbons, and is absent when a triple bond is present;
R₁₃ is COOR₇, CH₂OH, CHO, tetrazole, NHSO₂R₁₄, hydroxymethylketone, CN, or CON(R₇)₂;
each R₁₄ is independently OH, alkyl or alkoxy of 1 to 6 carbon atoms, perhaloalkyl of 1 to 6 carbon atoms, phenyl or phenyl substituted by alkyl or alkoxy groups of 1 to 3 carbon atoms, halogen, hydroxy, haloalkyl, COOH, CN, formyl or acyl of 1 to 6 carbon atoms;
X is O, S, SO or SO₂;
each Y is independently O, S, SO, SO₂,

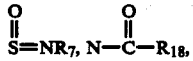

or N—CN;
Z is =C(R₇)₂ or O;
m is 0 or 1;
n is 0 or 1 provided that both m and n are not O, or that both m and n are not 1;
t is 1 or 2, provided that one but not both Z units is —C(R₇)₂ when t is 2;
p is 0 or 1;
q and r are each independently 0 to 20 provided that the total of q and r does not exceed 20;
and pharmaceutically acceptable salts thereof.

2. Compounds of claim 1 having the formula:

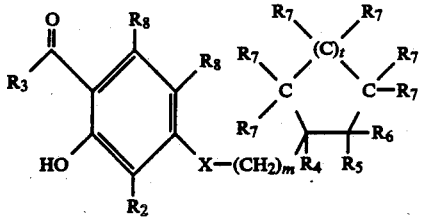

wherein:
R₄ is H; OH, provided that m is 1; or

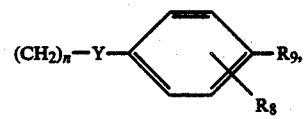

provided that both m and n are not zero;
R₅ is H; OH, provided that R₆ is not OR₁; or

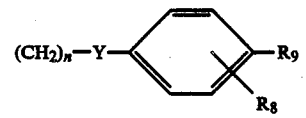

R₆ is H; OH; or

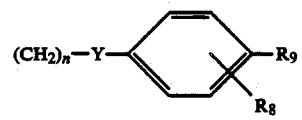

R₉ is

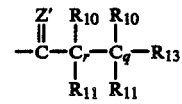

wherein:
Z' is O, or H and OH;
q and r are each independently 0 to 5;
Y is O, S, SO or SO₂; and
R₂, R₃, R₇, R₈, R₁₀, R₁₁, R₁₃, X, t, and m are as defined in claim 1.

3. A method of treating the conditions of asthma, allergic reactions, and inflammation comprising administering a therapeutically effective dosage of a compound of claim 1 to a mammal suffering from one or more of said conditions.

4. A method of claim 3 wherein the mammal is a human.

5. A composition for antagonizing leukotriene action in a mammal comprising an amount of a compound of claim 1 effective as a leukotriene antagonist and a pharmaceutically acceptable carrier.

6. A method of antagonizing leukotriene action in a mammal which comprises administering to said mammal an amount of a compound of claim 1 effective as a leukotriene antagonist.

7. A method of claim 6 wherein the mammal is a human.

8. A method of inducing cytoprotection in a mammal comprising administering to a mammal a cytoprotective amount of a compound of claim 1.

* * * * *